(12) United States Patent
Benyaminpour et al.

(10) Patent No.: US 10,172,739 B2
(45) Date of Patent: Jan. 8, 2019

(54) PORTABLE THERAPEUTIC SYSTEM USING HOT OR COLD TEMPERATURE

(71) Applicants: Behrouz Benyaminpour, Great Neck, NY (US); Jim Benjamin, Great Neck, NY (US); Ramin Benjamin, Great Neck, NY (US)

(72) Inventors: Behrouz Benyaminpour, Great Neck, NY (US); Jim Benjamin, Great Neck, NY (US); Ramin Benjamin, Great Neck, NY (US)

(*) Notice: Subject to any disclaimer, the term of this patent is extended or adjusted under 35 U.S.C. 154(b) by 1023 days.

(21) Appl. No.: 13/941,338

(22) Filed: Jul. 12, 2013

(65) Prior Publication Data

US 2014/0303698 A1    Oct. 9, 2014

Related U.S. Application Data

(60) Provisional application No. 61/670,719, filed on Jul. 12, 2012.

(51) Int. Cl.
| | |
|---|---|
| *A61F 7/02* | (2006.01) |
| *A61F 7/00* | (2006.01) |
| *A61F 7/03* | (2006.01) |
| *A61F 7/10* | (2006.01) |

(52) U.S. Cl.
CPC .............. *A61F 7/02* (2013.01); *A61F 7/0085* (2013.01); *A61F 7/03* (2013.01); *A61F 7/106* (2013.01); *A61F 2007/0054* (2013.01); *A61F 2007/0055* (2013.01); *A61F 2007/0057* (2013.01); *A61F 2007/022* (2013.01); *A61F 2007/0219* (2013.01); *A61F 2007/0222* (2013.01); *A61F 2007/0223* (2013.01); *A61F 2007/0228* (2013.01); *A61F 2007/0231* (2013.01); *A61F 2007/0246* (2013.01); *A61F 2007/0247* (2013.01); *A61F 2007/0249* (2013.01); *A61F 2007/0253* (2013.01)

(58) Field of Classification Search
CPC ................. A61F 2007/0054; A61F 2007/0056
See application file for complete search history.

(56) References Cited

U.S. PATENT DOCUMENTS

| | | | |
|---|---|---|---|
| 4,184,537 A | 1/1980 | Sauder | |
| 4,738,119 A * | 4/1988 | Zafred | ............... A41D 13/0053 2/81 |

(Continued)

FOREIGN PATENT DOCUMENTS

| | | |
|---|---|---|
| WO | WO 2005/112675 A1 | 12/2005 |
| WO | WO 2008/129357 A2 | 10/2008 |

(Continued)

*Primary Examiner* — Kaitlyn Smith
(74) *Attorney, Agent, or Firm* — Ted Whitlock (57) ABSTRACT

Disclosed is a system which employs a cooling or heating pad which is preferably a thin, flexible pad for placement at an intended area of the body. The pad includes a layer of highly conductive material which can be cooled or heated using a portable source of heat or cold material delivered to the conductive material by a delivery conduit. Valves can be included to regulate flow of the cooling or heating material from the source to the pad. The system can also include a dual-chambered canister for containing two different media for heating, cooling or for alternating heating and cooling the pad.

7 Claims, 4 Drawing Sheets

(56) References Cited

U.S. PATENT DOCUMENTS

| | | | | |
|---|---|---|---|---|
| 4,846,176 A * | 7/1989 | Golden | A61F 7/02 165/46 |
| 5,534,021 A * | 7/1996 | Dvoretzky | A61F 7/02 126/204 |
| 5,643,336 A * | 7/1997 | Lopez-Claros | A61F 7/02 126/204 |
| 5,755,275 A * | 5/1998 | Rose | A61F 7/02 165/171 |
| 5,755,755 A * | 5/1998 | Panyard | A61F 7/02 607/104 |
| 5,871,526 A * | 2/1999 | Gibbs | A61F 7/02 165/46 |
| 5,888,185 A * | 3/1999 | Regan | A61F 7/02 600/15 |
| 6,074,414 A * | 6/2000 | Haas | A61F 7/02 607/108 |
| 6,197,045 B1 * | 3/2001 | Carson | A61F 7/02 601/148 |
| 6,221,275 B1 * | 4/2001 | Choi | C09K 5/10 165/104.19 |
| 6,375,674 B1 * | 4/2002 | Carson | A61F 7/0085 5/422 |
| 7,367,341 B2 * | 5/2008 | Anderson | A61B 5/415 128/898 |
| 7,527,612 B1 * | 5/2009 | Carpenter | A61F 7/02 604/291 |
| 8,052,628 B1 * | 11/2011 | Edelman | A61F 7/02 602/19 |
| 8,192,474 B2 * | 6/2012 | Levinson | A61F 7/007 607/100 |
| 8,491,644 B1 | 7/2013 | Carson | |
| 2001/0018605 A1 | 4/2001 | Helming | |
| 2003/0055475 A1 * | 3/2003 | Rousmaniere | A61F 7/034 607/114 |
| 2003/0220674 A1 * | 11/2003 | Anderson | A61B 5/415 607/96 |
| 2005/0107855 A1 * | 5/2005 | Lennox | A61F 7/10 607/104 |
| 2006/0142828 A1 * | 6/2006 | Schorr | A61F 7/034 607/108 |
| 2007/0010861 A1 * | 1/2007 | Anderson | A61B 5/415 607/96 |
| 2008/0077202 A1 * | 3/2008 | Levinson | A61F 7/02 607/96 |
| 2008/0082151 A1 * | 4/2008 | Quincy | A61F 7/034 607/96 |
| 2008/0103567 A1 * | 5/2008 | Augustine | A61F 7/007 607/108 |
| 2008/0147152 A1 * | 6/2008 | Quincy | A61F 7/03 607/112 |
| 2008/0255644 A1 * | 10/2008 | Carson | A61F 7/10 607/104 |
| 2009/0062892 A1 * | 3/2009 | Ilcheva | A41D 13/0518 607/108 |
| 2009/0099631 A1 * | 4/2009 | Augustine | A61F 7/007 607/104 |
| 2009/0216305 A1 * | 8/2009 | Bonner | A41D 13/1254 607/108 |
| 2009/0235680 A1 | 9/2009 | Serrano Molina | |
| 2010/0018682 A1 * | 1/2010 | Goldmann | A41D 13/0053 165/104.31 |
| 2010/0100090 A1 * | 4/2010 | Rose | A61F 7/10 606/22 |
| 2010/0204763 A1 * | 8/2010 | Augustine | A61F 7/007 607/96 |
| 2011/0313497 A1 * | 12/2011 | McFarlane | A61F 7/02 607/109 |
| 2012/0089208 A1 * | 4/2012 | York | A61N 5/0625 607/100 |
| 2012/0215293 A1 * | 8/2012 | Fruitman | A61F 7/02 607/96 |
| 2013/0066309 A1 * | 3/2013 | Levinson | A61F 7/007 606/20 |
| 2013/0253496 A1 * | 9/2013 | Anderson | A61B 5/415 606/21 |
| 2014/0303698 A1 * | 10/2014 | Benyaminpour | A61F 7/02 607/107 |
| 2014/0371732 A1 * | 12/2014 | Rose | A61F 7/10 606/23 |
| 2015/0157495 A1 * | 6/2015 | Robst | A61F 7/0085 607/104 |
| 2015/0209174 A1 * | 7/2015 | Abreu | A61F 7/02 607/104 |
| 2015/0328077 A1 * | 11/2015 | Levinson | A61F 7/007 607/96 |

FOREIGN PATENT DOCUMENTS

WO    WO 2009/056296 A1    5/2009
WO    WO 2014/055082 A2    4/2014

* cited by examiner

PORTABLE THERAPEUTIC SYSTEM USING HOT OR COLD TEMPERATURE

CROSS-REFERENCE TO RELATED APPLICATION

This is a continuation-in-part claiming the benefit of and priority to U.S. Provisional Patent Application, Ser. No. 61/670,719 filed Jul. 12, 2012.

BACKGROUND OF THE INVENTION

Cooling or heating pads are well known in the art and have been used for therapeutic procedures for many years. Currently available cooling or heating pads typically require prior refrigeration/freezing or heating/warming of the pad, as the case may be, and can require more than one pad so that a "reserve" pad can be refrigerated/frozen ("cooled") or heated while another is in use. In addition, such pads typically use bulky materials which prohibit free mobility of the injured area and can be uncomfortable to wear during normal activities.

Cooling or heating pads in the prior art generally employ a gel or similar material to retain externally-generated cold or heat, whereby the cooled or heated pad is placed within the source of cold or heat (e.g., refrigerator/freezer or oven, such as a microwave oven) and is removed from the cold or heat source so that it can be applied to an intended area of the body in need of treatment using cold or hot temperatures.

The prior art, and the disadvantages thereof, is discussed here in the context of cool or cold packs and therapy but, as would be understood by persons of ordinary skill in the art, apply equally to heat or hot-packs and therapy. For example, a common method of alleviating pain or swelling after a surgical procedure or accidental injuries is to use a cold compress, using an ice bag, a bag of frozen peas, or snow-type freezer packs to be wrapped around or applied to the affected area. Currently available cooling pads require pre-cooling or pre-freezing of the pad whereby the pad is physically placed within the cold source prior to use.

Other cooling devices utilize cold liquid to circulate around the affected area and require tubes carrying the liquid to be continuously connected to the device whereby use of the device is inconvenient and bulky.

Moreover, bulky cooling pads or cold packs are limited as to their applicability to certain parts of the body. For example, specific areas of the face, such as the brow or nose, generally require the pad or pack to cover the whole, general area and cannot provide a truly moldable device which substantially conforms to areas of the body which are not easily enwrapped.

A pad which is pre-cooled or frozen generally adapts its shape to the environment of the cold source. For example, even a flexible ice pack, when frozen, is generally defined by the shape of its outer container. When placed in a freezer, ice packs are typically formed in a generally rectangular shape with generally flat faces for contacting the body. Although they can be frozen in a particular or pre-formed "curved" shape, it is well recognized that the curvature only generally mimics the shape of the body at the site of application and does not mold to the specific contours as would be desired.

The previously available processes, though effective, are inconvenient and can limit mobility of the person due to the weight or bulkiness of the ice or cooling pack. None of the previous devices known to the inventors can provide cold therapy "on demand" without requiring removal of the pad to replace cold or hot temperatures, and without the use of bulky materials or requiring continuous circulation of liquid through the device during use.

Thus, what is needed is a flexible or moldable cooling or heating pad device and system that can efficiently provide cold or heat to a specific area of the body. Preferably, this desired action is achieved by a system comprising a pad that can be "charged" with cold or heat at the time of use and at the site of use so that the pack does not require extended periods of time to cool down or become frozen, or to warm up to a desirable temperature before use. Neither would such system require removal of the pad for re-cooling, re-freezing, or re-heating following dissipation of the therapeutically effective cold or hot temperature after a period of time.

Moreover, what is needed is a system which can provide a "re-chargeable" pad which can be re-cooled or re-heated during use without requiring connection to an external source or generator of cold or hot temperatures. Thus, a pad and system providing an external source of cold or heat which is connected to the pad temporarily, only to provide cold or heat to the pad, and then is disconnected from the pad during use, advantageously provides greater mobility and ease of use to and for the user of such pad and system.

These advantages, as described herein, as well as other advantages that would be recognized and appreciated from this disclosure, are achieved by the subject invention which overcomes the disadvantages and inconvenience of cold and heat packs known or currently available in the art.

SUMMARY OF THE INVENTION

The subject invention provides a system and method for cooling or heating an area of the body which is advantageously safe, convenient, portable, and is compact in that it does not require the use of bulky materials. The system and method comprise a thin, flexible pad or "wrap" comprising a highly efficient temperature-conducting material which can be activated to provide cold therapy or heat therapy on-demand. The system and method of the invention further comprise a portable source of endothermic (cooling) or exothermic (heating) medium to cool or heat the pad. The heating or cooling medium can be delivered to the pad via a conduit, such as a connecting rod or tube, which has a connecting means at one end compatible with and engaging or adjoining to the source of the heating or cooling medium, and a second connecting means at its other end compatible with and adjoining to the conductive material of the pad.

In summary, the invention comprises a portable heating or cooling pad system for applying hot or cold temperature to an area of a body in need of treatment using hot or cold temperature, the system comprising:

a thin, flexible pad comprising a layer of highly efficient temperature-conductive material;

a detachable delivery conduit for delivering the heating or cooling medium from a source to the conductive material; and a portable source of cooling or heating medium within a container, said medium being deliverable to the temperature-conductive material by the removable delivery conduit, as desired, to cool or heat the conductive material and pad for use.

The conductive material and pad is cooled or heated at the site of use without requiring removal of the pad or without requiring continuous circulation of the medium from the source to the pad during use.

The system can further comprise a connecting conduit engaged or integral therewith. The connecting conduit can be a hollow tube or a solid rod. Preferably, the connecting conduit further comprises a delivery port for receiving a cooling or heating medium.

The source of cooling or heating medium is a canister capable of holding the cooling or heating medium under pressure, and preferably comprises a nozzle in communication with a chamber within the canister and outside the canister, allowing delivery of the medium to the conductive material. The nozzle preferably comprises a valve for regulating flow of pressurized cooling or heating medium from the canister.

The heating or cooling medium is a medium providing exothermic or endothermic conditions to the conductive layer or material, and is typically a cooling medium such as liquid nitrogen, Freon gas, or the like.

The system employs a heating or cooling pad for applying hot or cold temperature to an area of a body in need of treatment using hot or cold temperature. Preferably, the pad comprises a thin, flexible layer of highly efficient temperature-conductive material heated or cooled by an external heating or cooling medium deliverable to the conductive material while the pad is in use on the body. The heating or cooling medium can be delivered to the conductive material or layer by way of a connecting conduit engaged with or connected to the conductive material.

The connecting conduit can further comprise a delivery port for receiving the heating or cooling medium, whereby the delivery port is engaged or integral with, or connected or affixed to, the connecting conduit.

The heating or cooling pad can further comprise a protective cover surrounding the conductive material. The covering material can comprise any material typically used for protection when applied next to the skin of a user, and can be present for purposes of protecting the conductive material from perspiration, oil, or compositions applied to the skin.

Alternatively, the pad can comprise an outer cover on one face of the conductive material. For example, the cover can be over an inner face of the pad contacting the skin of the user, or can cover on an outer face of the pad, the outer face being opposite a face contacting the skin.

The covering over the inner face can comprise a material which allows heat or cold transfer from the conductive material to a surface of the cover. Preferably, such cover material is a polymeric or textile material. The covering over the outer face of the conductive material preferably comprises an insulating material for retaining or directing the heat or cold to toward the skin of the user. The insulating material can be a porous or non-porous polymeric material having temperature insulating properties. Porous material can be the result of pores formed naturally in the manufacture of the material or can be formed by physical formation of pores in a non-porous material. For example, micro-pores can be formed in a non-porous material using a laser drill.

Preferably, the heating or cooling pad comprises a temperature conductive material, such as graphene, aluminum oxide, or the like. These conductive materials can be provided as solid "plates", powder, beads, or "fibers." When the conductive material is a powder or beads, it is preferred that the material is contained within a thin bladder forming the pad. The conductive material can be used alone or in combination with a gel composition, as known in the art for use with heating or cooling pads.

For securing the pad in position in relation to the area of the body in need of treatment, the pad can further comprise an attachment means. The attachment means can be affixed to the pad or a cover of the pad. As recognized in the art, the attachment means can be any suitable and available strap, buckle, snap, or hook and loop material.

A further embodiment of the invention comprises a canister for containing two media for heating or cooling. The canister comprises an outer housing wall bounding a two chambers within the canister, said two chambers formed by a longitudinally oriented dividing wall within the canister and defining first and second chambers. The first and second chambers independently contain a first and second medium wherein said first and second media are selected from (a) an endothermically reacting media forming a cooling medium when mixed together, (b) an exothermically reacting media forming a heating medium when mixed together, or (c) a cooling medium in the first chamber and a heating medium in the second chamber.

The canister can comprise first and second nozzles, wherein the first nozzle communicates from outside the canister to inside the first chamber, and the second nozzle communicates from outside the canister to the second chamber. The canister can further comprise a valve for regulating flow of cooling or heating media from within a chamber of the canister.

Use of the system of the invention provides an advantageous method of providing heat or cold therapy to an area of a body. Specifically, the method of the invention comprises the steps of:
   (a) providing a thin, flexible pad comprising a layer of highly efficient temperature-conductive material;
   (b) applying the pad to the area of the body in need of heat or cold therapy; and
   (c) cooling or heating the temperature-conductive material using a cooling or heating medium from an external source to cool or heat the temperature-conductive material and thereby cool or heat the pad.

A preferred method is carried out whereby the conductive material is cooled using liquid nitrogen. Alternatively, the method can advantageously employ alternating heat and cold therapy using the pad without removing the pad between heat and cold therapies.

The subject invention can advantageously be used at very specific areas of the body. Preferred embodiments of the subject invention provide a cooling or heating surface which can be contoured or molded to curvatures of the affected area such as such as a knee, ankle, shoulder, or smaller area such as the bones around the eye or nose, or any other part of the body as needed.

Due to the portability of the pad and cooling or heating medium, an individual using the system or carrying out a therapeutic method using the system can advantageously continue all normal activities while wearing the pad, and can re-cool or re-heat the pad without removing the pad when the heat or cold dissipates.

The heating or cooling medium can advantageously be delivered to the conductive layer as desired, or "on demand", by a user, for example, by a connecting means which is in removable communication with a source of heat or cold medium.

The method comprises providing a pad, as described above, contacting a temperature-conductive layer of the pad with a heating or cooling medium such that the outer surface of the pad becomes cold or hot as intended. The pad is then applied to the outer surface of the skin at an area of the body in need of such hot or cold treatment. The heating or cooling medium can be delivered to the conducting layer of the pad by a tube or conduit in communication therewith. For example, for delivering a cooling medium to the conducting layer, a stand-alone or portable canister of liquid nitrogen or other liquid, gas (e.g., Freon) or solid (preferably, fluid) can be used.

More preferably, the canister or communicating tube or conduit comprises a valve for regulating the flow of medium to the conductive layer, including a shut-off position to completely stop the flow of medium to the conductive layer.

The subject system and method have numerous applications, including for post-surgical treatment of an area of the body, reduction of fever or hyper- or hypothermia conditions, for minimizing bruising, for emergency application in minimizing tissue damage following a heart attack, for fertility purposes (such as maintaining coolness in the groin or scrotal area).

A preferred device can be shaped to conform to a particular area of the body, and can be gender-specific, such as for women following breast augmentation procedures, or for men following vasectomy or hernia repair procedure. The malleability or molding capability of the pad to conform to a specific area of the body is facilitated by the portability of the pad. Specifically, the pad can be placed at the site to contact the body in a form-fitting manner, then frozen in situ using the cold or heat medium. This is advantageous over conventional freezer packs which are only generally contoured to fit the specific area of the body by being frozen in a freezer, then removed to be placed onto the area of the body.

In addition, the subject invention contemplates incorporating the pad into or as part of clothing, including underwear or outer apparel. Outer apparel can include sports uniforms or protective gear, or military uniforms.

Another advantage of the subject invention is that the conducting material of the pad can receive either one of a heating or cooling medium, such that the therapies can be interchanged, for example, alternating heat or cold for using both therapies on the same area of the body, without changing or replacing the pad between therapies.

As a further aspect of the invention, a dual-chambered canister can be used as a source of heating or cooling medium for the desired treatment or for alternating heat and cold treatments. One embodiment of the invention includes a dual-chambered canister having a first chamber containing a cold-temperature or cooling medium, and a second chamber containing a hot-temperature or heating medium.

It is therefore an object of the subject invention to provide a convenient and portable means of cold (or heat) therapy which overcomes certain disadvantages of the currently available cooling or heating pads. Advantageously, a device in accordance with the subject invention is lightweight, substantially compact, and portable.

It is a further object of the invention to provide a pad and method for heat or cold therapy which does not require a continuous circulation of cold or hot liquid or fluid through the pad during its use on or around a body part.

The design and contour of the pad comprises a relatively thin, flexible material which can allow the device to be molded to closely contour the shape or curvature of the treated area of the body, allowing the person to wear normal clothing and perform normal activities while the cool or hot therapy pad is in use. Further, the subject device and method do not require removal and replacement of the pad when further cooling or heating is desired.

DETAILED DESCRIPTION OF THE INVENTION

The subject invention provides a system and method for cooling or heating an area of the body using a flexible pad or "wrap" which can be activated on demand to provide cold therapy or heat therapy at a site or area of the body in need of heat or cold therapy. The system and method of the subject invention is advantageously safe, convenient, portable, and is compact in that it does not require the use of bulky materials.

The system of the subject invention comprises a heating or cooling pad which includes a heat or cold conductive material. The pad can advantageously be used at very specific areas of the body. A preferred embodiment of a pad of the subject invention has minimal thickness and high flexibility such that the pad can be contoured or molded to curvatures of a target area of the body, such as a knee, ankle, shoulder, or areas such as the bones around the eye or nose, or any other part of the body as needed.

Due to the portability of the system, the individual using the system or receiving the therapeutic method using the system can continue all normal activities while wearing the device.

The subject invention employs a cryo- or heat-therapy system or method employing a pad which comprises a highly efficient temperature-conducting material which can be activated by contacting the conducting material with a cooling or heating medium. The conductive material is preferably provided as a thin layer, bounded or covered by a polymeric material or textile which allows the cold or hot temperature to be carried from the conducting material to an outer surface of the pad, thereby cooling or heating the surface of the skin when contacted by the pad. The heating or cooling material can advantageously be delivered to the conductive layer as desired by a user, for example, by a connecting means which is in removable communication with a source of heat or cold medium.

For purposes of the subject invention, cooling or heating of the conductive material or pad comprising the conductive material, can be referred to as "charging" the conductive material or pad. Thus, re-cooling or re-heating of the conductive material or pad comprising the conductive material is referred to as 're-charging" the conductive material or pad comprising the conductive material.

The subject method comprises providing a pad comprising a temperature-conductive material described above, contacting the temperature-conductive material with the heating or cooling medium such that the pad is "charged" with heat or cold temperature, and the outer surface of the pad becomes cold or hot as intended. The pad is can then applied to the outer surface of the skin at an area of the body in need of such hot or cold treatment.

The heating or cooling medium can be delivered to the conductive layer by a tube or conduit in communication therewith. For example, for delivering a cooling medium to the conductive layer, a stand-alone or portable canister of liquid nitrogen or other cooling gas, liquid, or solid available or capable of being contained in a portable canister, can be used. Preferably, the canister or communicating tube or conduit comprises a valve for regulating the flow of medium to the conductive material or layer, including a shut-off position to completely stop the flow of cooling or heating medium to the conductive layer.

Figure 1:
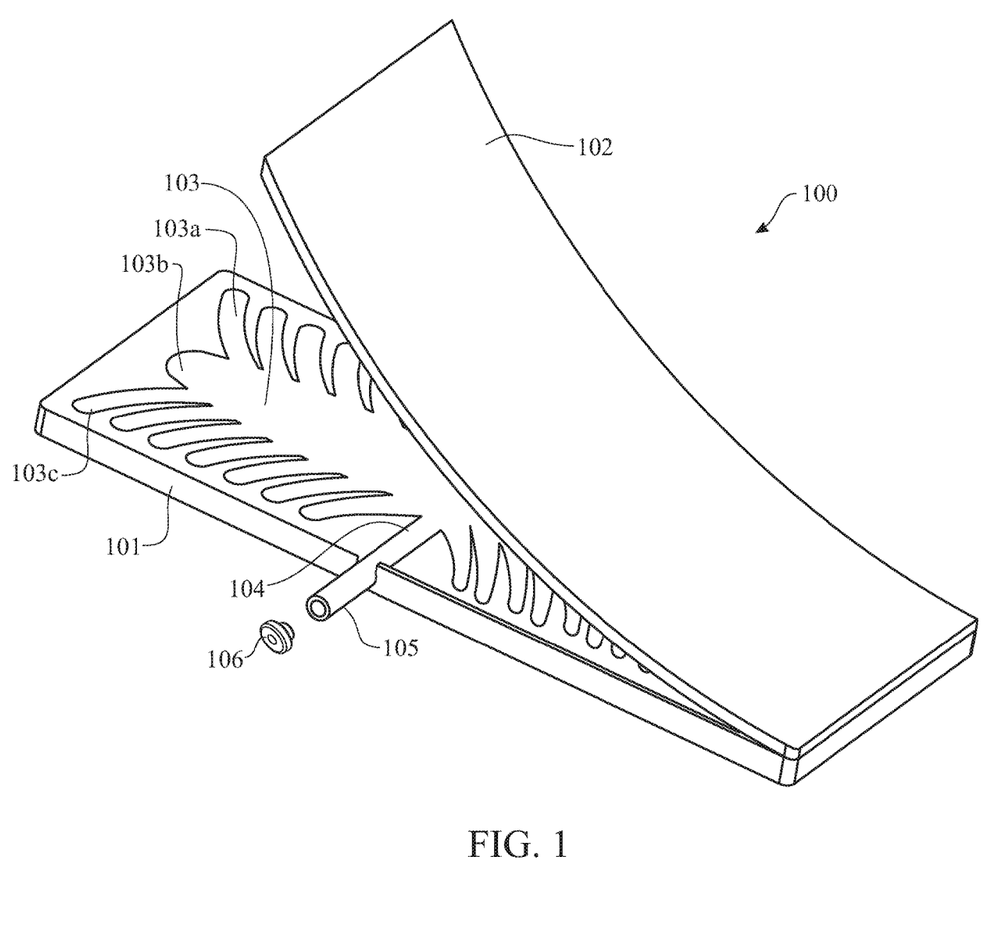
FIG. 1 shows an exploded perspective view of an embodiment of a pad of the invention, illustrating the conductive material layer, the outer covering, and charging conduit, including a charging port.

The subject system and its components can be readily understood by reference to the drawings attached hereto. FIG. 1 shows the cooling or heating pad 100 comprising two substrate layers 101 and 102 made from a flexible material and forming an outer cover for the pad. The flexible substrate materials can be a polymeric material or textile, and are preferably a material which is non-irritating or hypoallergenic to skin. The substrate layers can be the same or different. In one preferred embodiment, the substrate layers comprise a first substrate layer which is intended to contact the skin (the inner layer) and a second substrate layer forming the outer surface (non-skin-contacting). The substrate layer contacting the skin is preferably non-insulating, whereby the heat or cold is readily transferred from the pad to the skin and surrounding area. The outer layer is preferably insulating, whereby the cold or heat is prevented from dissipating from the pad to the outer environment, thereby retaining the heat or cold temperature within the pad, or actually serving to direct the heat or cold toward the skin surface. In one preferred embodiment, the outer substrate comprises pores, preferably micro-pores, that can allow gas and/or air pressure be relieved from the pad. Micro-pores can be formed in a substantially non-porous material by means of a laser drill. One advantage of a microporous outer substrate is the capability to relieve pressure without a valve.

Layered proximate to or between the substrate materials 101 and 102 forming a pad cover, is a highly efficient temperature-conductive material 103. The conductive material is preferably thin layer of a metal, carbon, or ceramic, such as graphene, or a material having temperature-conductive properties similar to graphene. Alternatively, the conductive layer can be a thin bladder containing within the bladder a highly conductive material such as aluminum oxide. Aluminum oxide can be provided as a powder, or small beads. Other temperature conductive materials, such as a polymeric gel, in the form of beads, or as a fluid, can also be included within the bladder, with or without aluminum oxide.

The conductive material is shown in FIG. 1 as having radiating extensions or "arms" 103a, 103b, and 103c, extending from a central core 103, to provide or distribute cold or heat to all areas of the pad within the cover. It would be understood that the conductive layer can be any shape, including rectangular, oval, circular, or amorphous, such that the heat or cold is provided to all areas of the pad, and preferably equally distributed to all areas of the pad.

In order to provide cold or heat to the conductive layer, the conductive layer is configured so that it can be in communication with an outside source of cold or heat, preferably an endothermic or exothermic medium serving as the cold or heat source, respectively. Cooling media useful in connection with the subject invention include, but are not limited to, inert gases (in gaseous, liquid or solid form) such as liquid nitrogen, argon, carbon dioxide (dry ice), chlorofluorocarbons, e.g., Freon, fluorocarbons such as pentafluoropropane, tetrafluoroethane, or the like, or conventional ice or gel. Heating media include any exothermic substance or mixture of substances which exothermically react in contact with one another.

Communication of heat or cold by a cooling or heating medium is achieved by a connecting conduit or connecting rod 104 integral with the conductive layer, for receiving a hot or cold medium. Connecting conduit 104 can be solid or tubular, and is also preferably flexible, malleable, or capable of being molded into shape by the user. When connecting conduit 104 is a hollow or tubular embodiment, the connecting conduit can further comprise a delivery port 105 at its receiving end, and delivery port 105 can further include a valve 106 for regulating flow of the hot or cold medium to the port, conduit, or conductive material or layer.

Also included in certain embodiments of a system in accordance with the subject invention is a dual-chambered canister providing at least two heating or cooling media from a single source. Preferably, the dual-chamber canister allows the contents to be contained within the chambers under positive pressure, such that the contents readily exit the chambers when the pressure is released.

Figure 2:
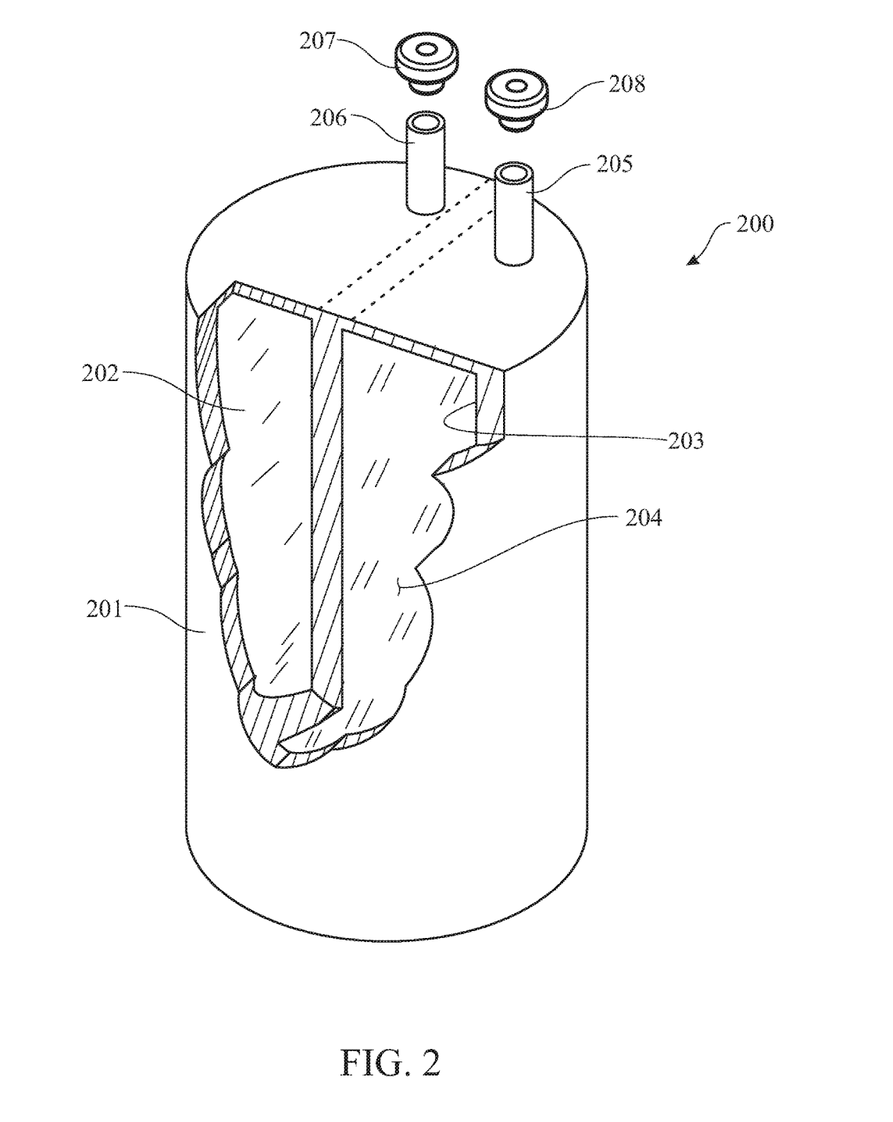
FIG. 2 shows a cutaway view of a dual-chambered canister of the invention.

One embodiment of a dual canister is shown in FIG. 2. The canister 200 comprises an outer containing wall 201 housing a first chamber 202 and a second chamber 203 which are completely separated from one another by a dividing barrier or wall 204 within the canister.

Each chamber can contain different cooling or heating media or each chamber can contain a portion of two media which, when mixed, provide a single heating or cooling medium. In one preferred embodiment, a cooling medium is contained within one of the chambers, e.g., 202, and a heating medium is contained within the other chamber, e.g., 203, or vice versa. This configuration allows a heat source and a cold source form a single canister. Alternatively, the respective chambers can each contain a separate fluid, liquid, solid, or gas which, when mixed together, endothermically or exothermically react with one another to form a cooling or heating medium which can be delivered to the device.

As further shown in FIG. 2, each chamber is independently in communication with the outside of the canister through a nozzle 205 or 206, which allows the contents of the chamber to exit the canister. More preferably, each nozzle 205 and 206 can comprise a valve, 207 or 208 to regulate the flow of the medium from the canister to the outside.

When two or more different media are mixed together to form an endothermic or exothermic reaction, the nozzles 205 and 206 can be connected or communicated to one another by a single mixing tube or conduit which can then engage or be connected to the connecting conduit 104 of the of the pad (see FIG. 1).

Figure 3:
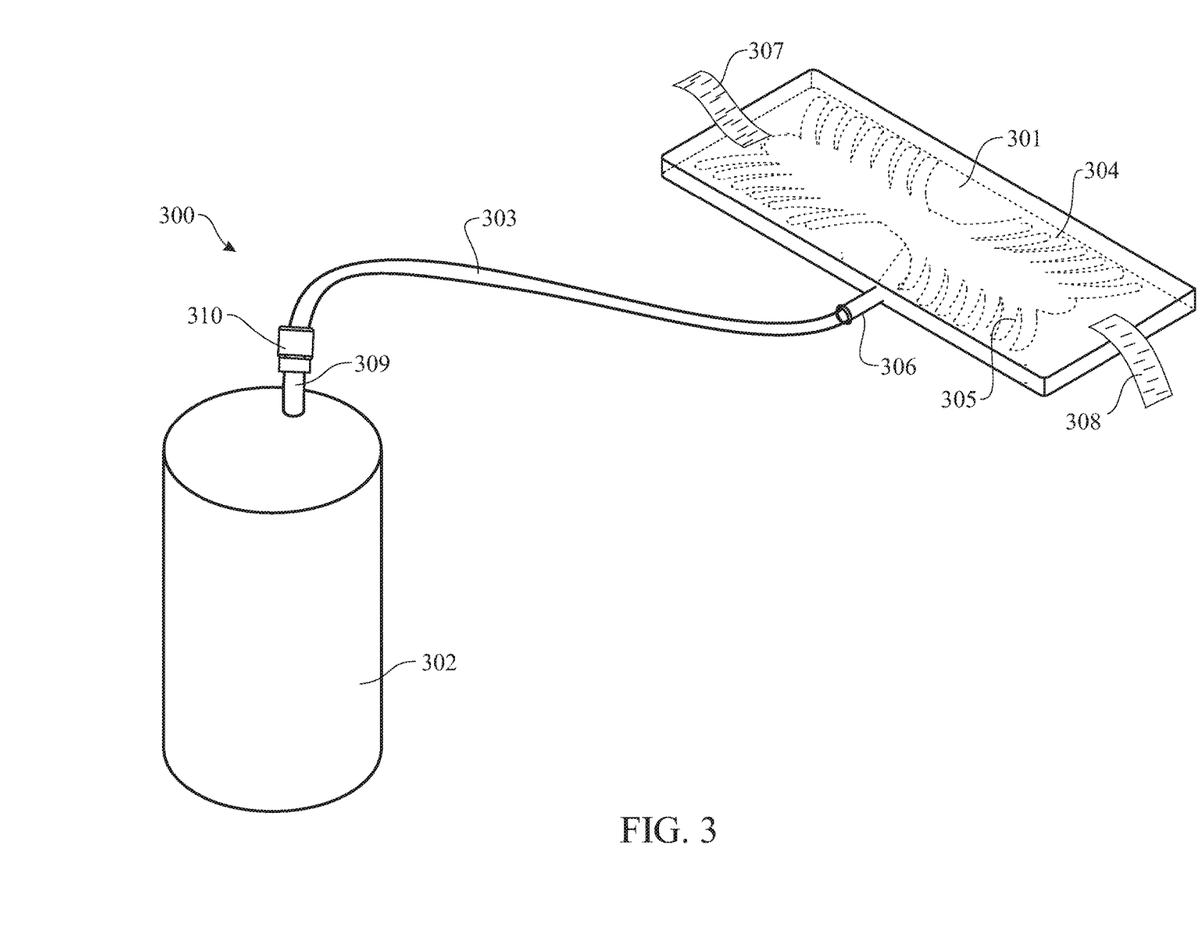
FIG. 3 illustrates an embodiment of the system and components thereof, including the pad, canister of heat or cold medium source, and delivery conduit.

FIG. 3 illustrates an embodiment of a system according to the subject invention, the system 300 comprising a pad 301, a portable canister 302 housing a heat or cold material as a source of heat or cold for the pad, and a delivery conduit 303 in communication with the pad 301 and canister 302 for delivery of heating or cooling medium to the pad from the source. In FIG. 3, pad 301 is further illustrated to comprise straps 307 and 308 for affixing or enwrapping the pad to the body area. A conductive layer 304 within the pad, is shown in broken lines since it is layered within the interior of the pad and is not seen from the outer surface. Also shown in broken lines is the connecting conduit or tube 305 by which cooling or heating media contact the conductive material 304. The connecting conduit 305 comprises a port 306 communicating the connecting conduit 305 with delivery conduit 303.

Delivery conduit 303 is connected at one end to port 306 of the pad 301, and is connected at its other end to the heating or cooling medium source. Delivery conduit 303 is typically connected to the pad and heating or cooling medium source only during the time of cooling or heating the conducting material within the pad and is removed and can be stored during use of the pad. Delivery conduit 303 serves to deliver heating or cooling medium from the source, e.g., canister 302, and connects to the canister nozzle 309. Alternatively, delivery conduit 303 can communicate with the canister nozzle 309 via a valve 310 connected to the canister nozzle 309.

Figure 4A:
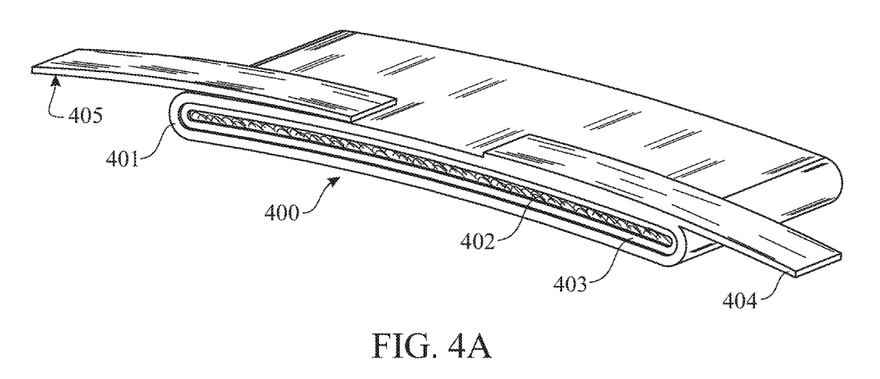
FIG. 4A shows a sectioned view of an alternative embodiment of a pad according to the subject invention wherein the conductive material or layer is provided within a bladder defining a chamber for containing or having its inner surface at least partially coated with the conductive material.
Figure 4B:
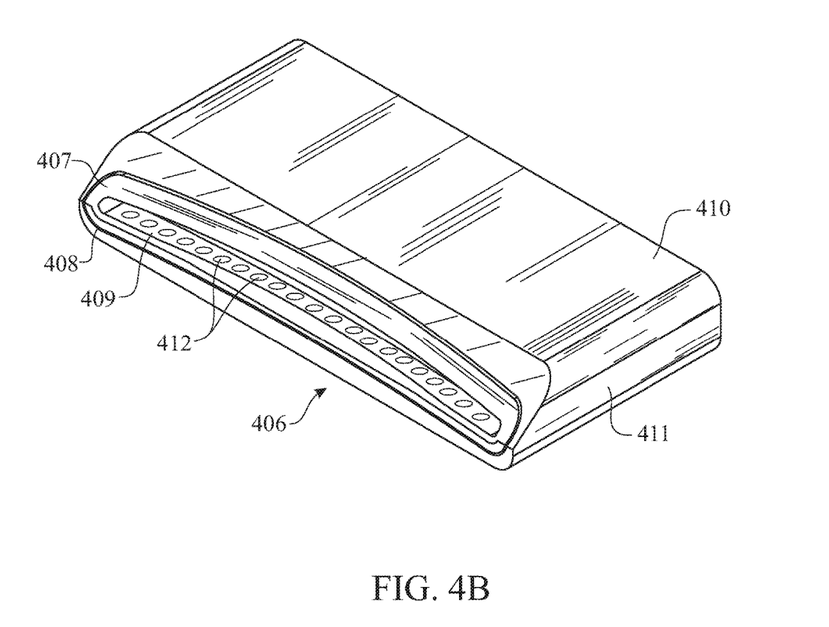
FIG. 4B shows a sectioned view of a pad embodiment comprising the bladder which can further include a gel or other conductive material in addition to the conductive layer on the inner surface of the bladder, and further comprising a protective cover layered over the top face and bottom face of the bladder.

An alternative embodiment of a pad according to the subject invention, wherein the conductive material or layer is provided as, or within, a bladder, is shown in FIGS. 4A and 4B. Specifically, FIG. 4A shows a pad 400 comprising a bladder 401 defining a chamber 402 for containing or having its inner surface at least partially coated with conductive material 403. The conductive material is shown here not to scale, and is typically a thin layer on the order of 0.1 to 5.0 millimeters in thickness.

The bladder 401 can be formed from any polymeric of textile material, and is preferably a flexible material, capable of being molded or contoured into a shape which fits the contours of the body part when in use. More preferably, the material used to form the bladder can provide the capability for the cold or heat within the bladder to be transferred easily and efficiently to the skin of the user when the pad is in use. The conductive material within the chamber of the bladder, or coating the inner walls of the bladder can be, for example, aluminum oxide, or other alloy, as would be recognized in the art.

The embodiment of the bladder pad of FIG. 4A is shown further comprising at least one attachment means, and is shown here having an attachment means 404 or 405 comprising two straps 404 and 405 which are affixed to the bladder or a covering thereof, and can encircle a body part and be affixed to one another to secure the pad in place on the body. As would be readily understood, the attachment means can be a single strap, such as an elastic band encircling the pad and allowing to be expandably enwrapping the body part, or can be more than one means, such as straps which are affixed together by an attachment means such as ties, hooks, buttons, snaps, or hook-and-loop material.

FIG. 4B shows a cooling or heating pad embodiment 406 comprising a bladder 407 defining a chamber 409. The inner surface of the bladder can comprise a layer of conductive material 408, and can further comprise additional conductive material 412, which can be gel or other heat or cold-retaining materials formed as beads or particles, or can be an amorphous fluid. The pad 406 can further comprise an outer covering. Preferably the outer covering includes an outer face 410 positioned to cover the top face (the outer face, not typically in contact with the skin), an inner face 411 positioned to cover the bottom face (inner face, contacting the skin) or both. When covering both faces, the outer cover can be formed as separate pieces adjoined together, or can be a single unitary piece covering at least the top and bottom faces of the bladder.

Generally, the covering serves as a protective layer, for the pad, the skin, or both. Accordingly, the material used is adapted for such use in accordance with its position. For example, a covering for the inner face contacting the skin can preferably be any polymeric or textile which can be comfortable in use, so long as it allows the cold or heat from the pad to transfer to the skin to carry out effective heat or cold therapy.

For the outer layer, a preferred material is an insulating material, e.g., a polymeric material which can prevent, reduce or retard loss of heat or cold from the pad. One preferred embodiment of a material used for an outer covering of a pad is a polymeric foam material, wherein air pockets are present within the material. Air is known as an effective heat or cold insulator and materials comprising air pockets, such as a bubble wrap material, are effective for such purposes.

The subject system, pad, and method have numerous uses and applications, including for post-surgical treatment of an area of the body, reduction of fever or hyper- or hypothermia conditions, for minimizing bruising, for emergency application in minimizing tissue damage following a heart attack, for fertility purposes (such as maintaining coolness in the groin or scrotal area). The device can advantageously be shaped to conform to a particular area of the body, and can be gender-specific, such as being shaped for women following breast augmentation procedures, or for men following vasectomy or hernia repair procedures.

The malleability or molding capability of the pad to conform to a specific area of the body is facilitated by the portability of the pad. Specifically, the pad can be placed at the site to contact the body in a form-fitting manner, then frozen in situ using the cold or heat medium. This is advantageous over conventional freezer packs which are only generally contoured to an area of the body by being frozen in that general contour shape in a freezer, then removed to be placed onto the area of the body.

In addition, the subject invention contemplates incorporating the device into, or as part of, articles of clothing, including underwear or outer apparel. Outer apparel can include sports uniforms or protective gear, or military uniforms.

The system of the invention, or components thereof, may be used by all military personnel who may be injured in line of duty. It provides quick and effective chilling temperature for the affected area. In some instances it may directly or indirectly allow freezing of the wounded body part to avoid profuse bleeding. The innovative function of this system is utilization of cold or hot temperature created or already in existence by means of liquid, gas, endothermic/exothermic chemicals, in the highly insulated canisters secured by highly conductive inner surface of the container or canister of any size.

Another advantage of the subject invention is that the device can receive either of a heating or cooling medium, such that the therapies can be interchanged, alternating heat or cold for both therapies to the same area of the body, without changing the device.

All embodiments of the single or dual chambered canisters can be refillable with the desired substance or substances. This allows for use of stand-alone or portable sources of cold and/or freezing (or heating) agent(s) with utmost comfort and convenience. The special design and contour of the device that comes in contact with the desired body part contains no bulky wrappings around the affected area and allows the person to wear normal clothing and conduct normal activities while the therapy is at work. It further does not require unwrapping and removal or replacement of the device during intermittent, periodic or continued use.

In preferred embodiments of the invention, the exterior surfaces can be insulated or comprise insulating material to avoid or reduce the time for dissipation of the temperature delivered to the conductive material or layer, thus providing extended use of the device without "re-charging" the temperature.

Other advantages and aspects of the invention include, but are not limited to, the following:

A) Outer layer—Not limited to a particular material or shape and can include a moldable gel material contained in a plastic housing fused or attached to the highly conductive surface whereby gel absorb and maintain the cold (or heat) from the conductive material and transmittable to the outer surface of the pad which can be applied to or placed in contact with the desired body surface. In some embodiments the conductive layer may be covered with a very fine and soft material not limited to conductive textiles readily available, or may be applied directly to the affected area.

B) Conductive Material or Layer—This layer consist of super conductive materials readily available and not limited to flexible or solid materials such as graphene or other materials currently used in geothermal technologies. Materials such as graphene can readily receive and transfer the cold (or the heat) with minimum loss from the source. This layer can be provided as different textures, sizes, or shapes according to the desired design, as would be recognized by persons of ordinary skill in the art. The conductive layer can also include a gel, liquid, solid or plasma. In addition, the conductive layer can further comprise an insulating material layered thereon, such as an insulating or reflective film or ceramic paint, or the like.

C) Outer Surface Material for Pad—The outer surface material used for the pad is not limited to plastic or any type of textile and preferably is an efficient conductor of heat or cold from the conductive material to the outer surface of the pad. The outer layer may be of porous or non-porous material that will allow dissemination of the cooling/heat producing gas or liquid without affecting the properties or allowing leakage of the content. In other embodiment of the invention, a connecting or fastening means, such as a strap, hook-and-loop fastening material, buckle, snaps, or other conventional fasteners, can be formed or provided integral with the cover material so that the device can be wrapped around a body part, such as a leg, arm, neck, or the like. An embodiment comprising a strap fastening means is illustrated in FIG. 3.

D) Delivery conduit—The delivery conduit can be provided in a variety of lengths as desired and serves to connect the cooling (or heating) material from its source to the conductive layer. The delivery conduit can be any shape (e.g., tubal or rectangular) and may be hollow or solid. One embodiment of the delivery conduit comprises a double tubing to allow faster circulation of the cooling or heating medium to all areas of the pad. The delivery conduit can comprise a highly conductive material or can be insulated using, for example, foam, Styrofoam or ceramic paint. Preferably, the delivery conduit comprises a fastening mechanism to engage with a port or nozzle of the cold/hot source. In other embodiments, the connective layer may be fused to the conductive layer.

E) The Cooling/Heating Source—The system comprising a cooling or heating source comprises, preferably a highly insulated container, such as a canister, that can hold a pressurized cooling or heating medium. A preferred cooling medium is liquid nitrogen, but can be carbon dioxide, alcohol, Argon gas, Freon gas, dry ice and or any other cooling substance (s) that may be in liquid, solid or gas form. Release of pressure on the container can cause the medium to exit the container, be carried through the delivery conduit to the connecting conduit and conductive material, whereby the pad surface is heated or cooled for use. In other embodiments, the container may hold highly active endothermic chemicals (or Exothermic to create heat) and may contain conductive gels. Upon excitement of the chemicals cold and freezing temperatures (or heat) will be generated. The container may also include a highly conductive rod that may be hollow or solid of any shape that is located in center of the container and will absorb and retains the cold (or heat). The current will then be transferred to the conductive layer of the pad by engaging it to conductive layer.

Alternatively, the source of cooling or heating can be provided by use of direct or indirect electrical or electromagnetic current, such as battery operated instrument to activate the conductive material within the pad.

It would be understood that the above description is representative of the and fully details the invention and its use. Other or additional embodiments would be recognized as within the scope, and are intended to be part of and included as part of the invention, without departing from the spirit of the invention.

The invention claimed is:

1. A portable heating or cooling pad for applying hot or cold temperature to an area of a body in need of treatment using hot or cold temperature, said pad consisting of a thin, flexible layer of highly efficient temperature-conductive material surrounded by flexible, porous substrate layers, the temperature-conductive material being heated or cooled by an external heating or cooling medium, deliverable to the temperature-conductive material through a delivery port engaged, connected, affixed or integral therewith, wherein the heating or cooling pad is capable of receiving the cooling or heating medium while the pad is in use on the body and wherein the porous substrate layers surrounding the temperature-conductive layer form a bladder containing a gel composition which retains heat or cold wherein the porous substrate layers allow for dissemination of the cooling or heating medium, the pad having an attachment means for positioning the pad in a fixed position in relation to the area of the body.

2. The heating or cooling pad of claim 1 wherein the attachment means is selected from the group consisting of a strap, buckle, snaps, or hook and loop material.

3. A portable heating or cooling pad for applying hot or cold temperature to an area of a body in need of treatment using hot or cold temperature, said pad consisting of a thin, flexible layer of highly efficient temperature-conductive material surrounded by flexible, porous substrate layers, the temperature-conductive material being heated or cooled by an external heating or cooling medium deliverable to the temperature-conductive material through a delivery port engaged connected, affixed or integral therewith, wherein the heating or cooling pad is capable of receiving the cooling or heating medium while the pad is in use on the body, wherein the porous substrate layers surrounding the temperature-conductive layer form a bladder containing a gel composition and wherein the porous substrate layers allow for dissemination of the cooling or heating medium, a cover having an inner face over a bottom face of the bladder and contacting skin of a user and an outer face over a top face of the bladder and opposite the inner face contacting the skin, the inner face of the cover comprising a material which allows heat or cold transfer from the conductive material to the inner face of the cover, and the pad having an attachment means for positioning the pad in a fixed position in relation to the area of the body.

4. The heating or cooling pad of claim 3 wherein the cover material is a polymeric or textile material.

5. The heating or cooling pad of claim 3 wherein the outer face is an insulating material for retaining or directing the heat or cold toward the skin of the user.

6. The heating or cooling pad of claim 5 wherein the insulating material is a porous or non-porous polymeric material having temperature insulating properties.

7. The heating or cooling pad of claim 6 wherein the insulating material is porous, comprising micro-pores.

* * * * *